(12) United States Patent
Justus

(10) Patent No.: US 9,867,944 B1
(45) Date of Patent: Jan. 16, 2018

(54) MULTI-MODE MEDICATION DISPENSER

(71) Applicant: Matthew L Justus, Piney Flats, TN (US)

(72) Inventor: Matthew L Justus, Piney Flats, TN (US)

(*) Notice: Subject to any disclaimer, the term of this patent is extended or adjusted under 35 U.S.C. 154(b) by 370 days.

(21) Appl. No.: 14/657,453

(22) Filed: Mar. 13, 2015

Related U.S. Application Data

(60) Provisional application No. 61/954,073, filed on Mar. 17, 2014.

(51) Int. Cl.
*A61M 5/32* (2006.01)
*A61M 5/24* (2006.01)
*A61M 5/28* (2006.01)
*A61M 5/315* (2006.01)

(52) U.S. Cl.
CPC ...... *A61M 5/2455* (2013.01); *A61M 5/31501* (2013.01); *A61M 5/31511* (2013.01); *A61M 5/31591* (2013.01)

(58) Field of Classification Search
CPC .. A61M 2005/2403; A61M 2005/2407; A61M 2005/3117; A61M 2005/3118; A61M 2005/312; A61M 2005/2474; A61M 5/2422; A61M 5/28; A61M 5/281; A61M 5/24; A61M 5/31511
See application file for complete search history.

(56) References Cited

U.S. PATENT DOCUMENTS

| | | | | |
|---|---|---|---|---|
| 5,997,512 A | * | 12/1999 | Shaw | A61M 5/3232 604/195 |
| 2005/0119623 A1 | * | 6/2005 | Pessin | A61M 5/326 604/198 |
| 2012/0109072 A1 | * | 5/2012 | Tabata | A61M 5/28 604/192 |
| 2013/0331798 A1 | * | 12/2013 | Tachikawa | A61M 5/28 604/218 |

* cited by examiner

*Primary Examiner* — Rebecca E Eisenberg
(74) *Attorney, Agent, or Firm* — Peter J. Van Bergen

(57) ABSTRACT

A medication dispenser includes a hollow body having an open first end and a second end opposing the first end. A hollow open-ended tube is coupled to the second end of the hollow body. A vial having one end sealed with a piston and one end sealed with a rupturable element is slidably disposed in the hollow body with the rupturable element being adjacent to one open end of the tube. A plunger body is indexed to an outer surface of the hollow body for axial movement with respect thereto. The plunger body includes a rod disposed therein for engaging the piston in the vial. An amount of medicine can be provided in the vial.

20 Claims, 5 Drawing Sheets

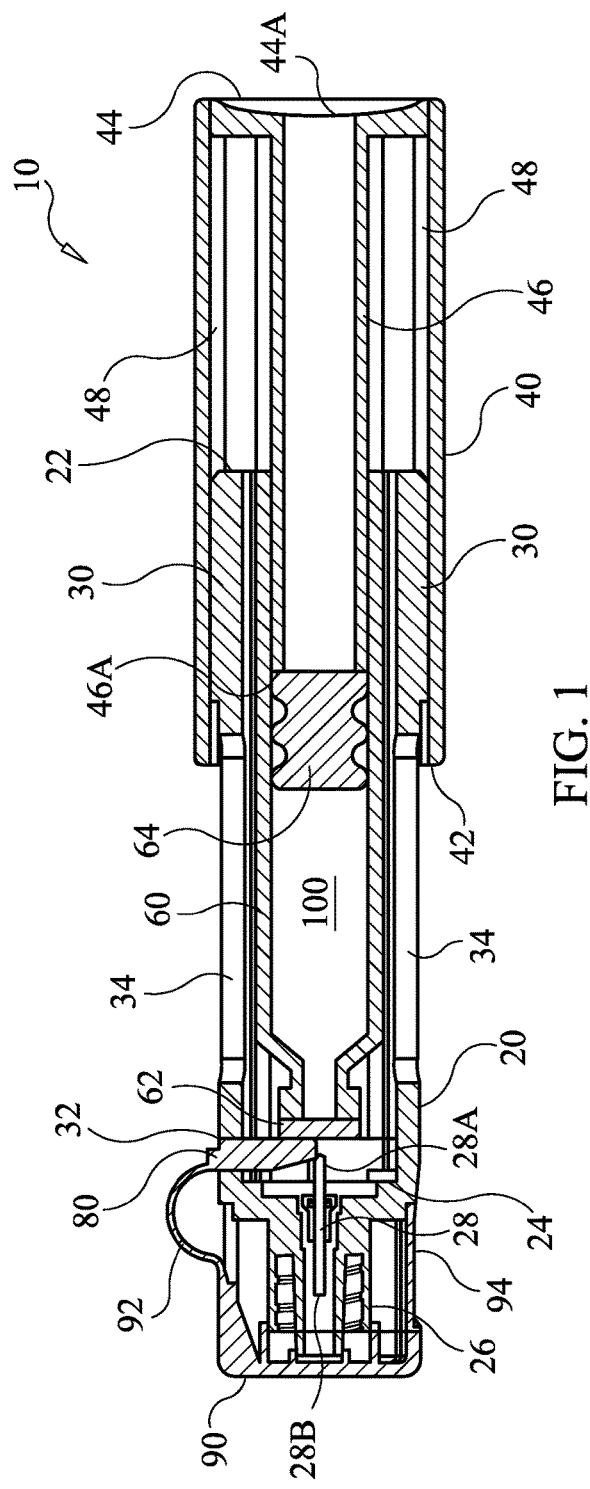
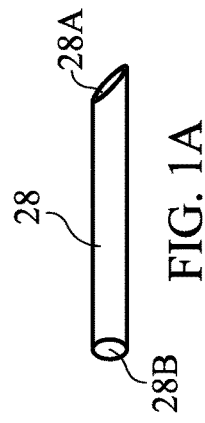
FIG. 1
FIG. 1A

MULTI-MODE MEDICATION DISPENSER

Pursuant to 35 U.S.C. § 119, the benefit of priority from provisional application 61/954,073, with a filing date of Mar. 17, 2014, is claimed for this non-provisional application.

FIELD OF THE INVENTION

The invention relates generally to medication dispensers, and more particularly to a pre-filled medication dispenser for dispensing medication via one of a variety of delivery modes.

BACKGROUND OF THE INVENTION

Administering medication via injection requires the filling of an injection needle's vial from a supply of medicine. However, in emergency and/or field situations, time and/or sanitation is compromised if an injection needle needs to be filled prior to use. Pre-filled single-dose injectors typically have a removable cap slid over the injector's needle. Unfortunately, existing pre-filled single-dose injectors are not robust enough for the rough handling that can be associated with emergency and/or field environments. Furthermore, there are other emergency and/or field applications that require medicine to be dispensed via an atomizer or intravenous drip line in which case the pre-filled needle-tipped injector is no longer of value.

SUMMARY OF THE INVENTION

Accordingly, it is an object of the present invention to provide a medication dispenser.

Another object of the present invention is to provide a medication dispenser that is readily adapted to disperse a medicine any of a variety of delivery modes.

Still another object of the present invention is to provide a medication dispenser whose integrity is maintained during pre-use handling thereof.

Other objects and advantages of the present invention will become more obvious hereinafter in the specification and drawings.

In accordance with the present invention, a medication dispenser includes a hollow body having a first end and a second end opposing the first end with the first end being open. A hollow open-ended tube is coupled to the second end of the hollow body. A vial having one end sealed with a piston and one end sealed with a rupturable element is slidably disposed in the hollow body with the rupturable element being adjacent to one open end of the tube. A plunger body is indexed to an outer surface of the hollow body for axial movement with respect thereto. The plunger body includes a rod disposed therein for engaging the piston in the vial. An amount of medicine can be provided in the vial.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 1 is a cross-sectional view of a multi-mode medication dispenser prior to the use thereof in accordance with an embodiment of the present invention;

FIG. 1A is an isolated perspective view of an embodiment of the open-ended tube used I the medication dispenser;

DETAILED DESCRIPTION OF THE INVENTION

Figure 2:
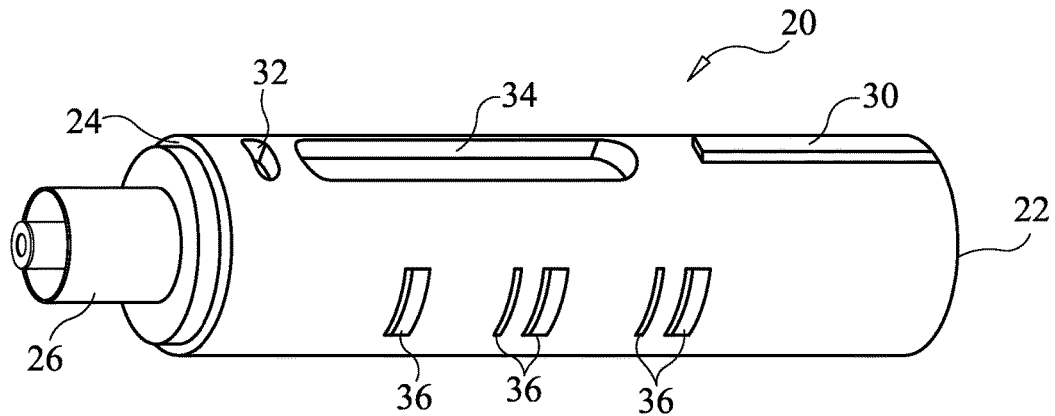
FIG. 2 is an isolated perspective view of the dispenser's body.
Figure 3:
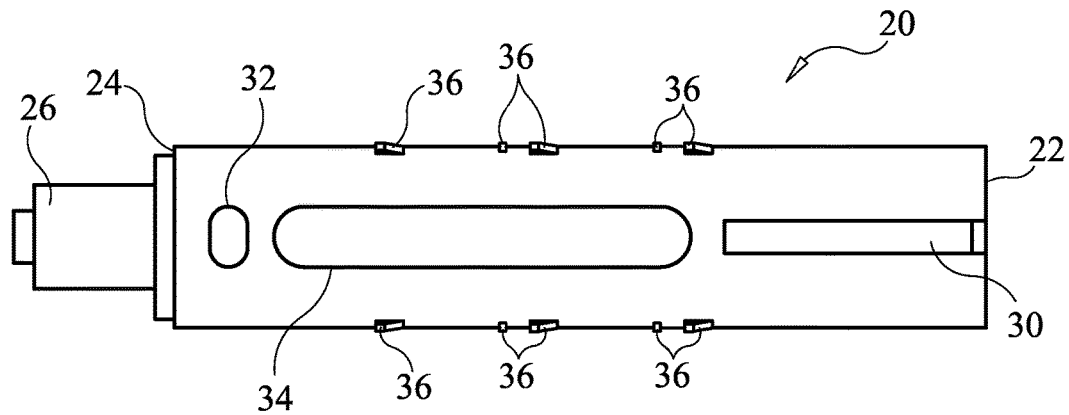
FIG. 3 is a side view of the dispenser's body.
Figure 4:
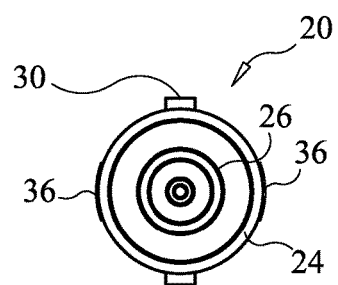
FIG. 4 is an end view of the dispenser's body from the luer fitting end thereof.
Figure 5:
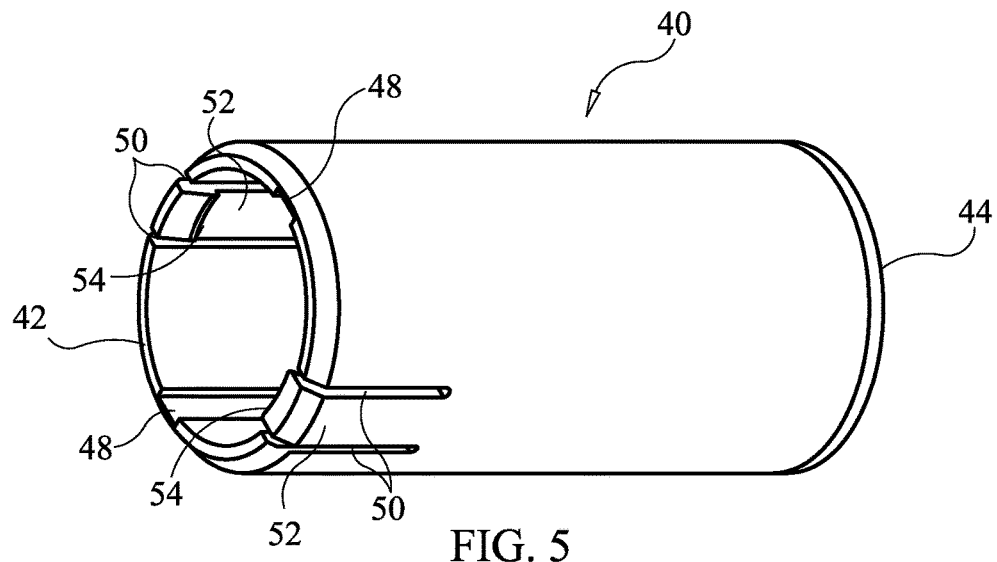
FIG. 5 is an isolated perspective view of the dispenser's plunger body.
Figure 6:
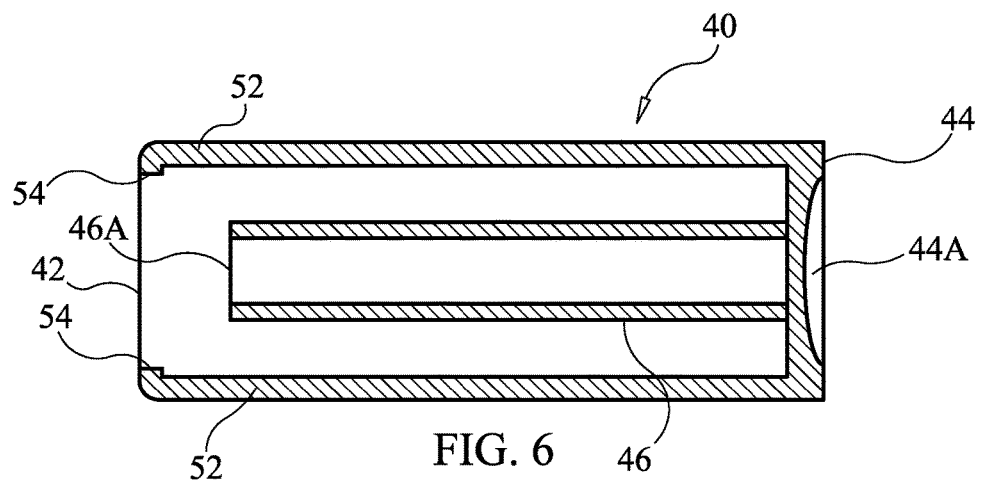
FIG. 6 is an axial cross-sectional view of the plunger body.
Figure 7:
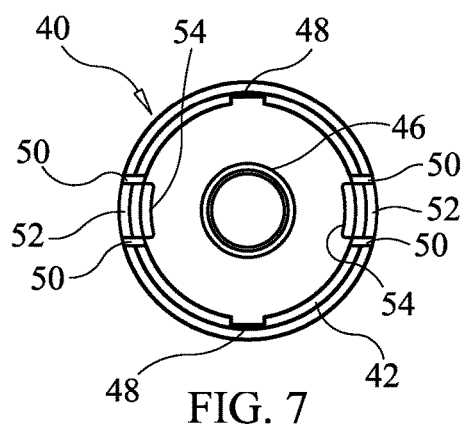
FIG. 7 is an end view of the plunger body from the open end thereof.
Figure 8:
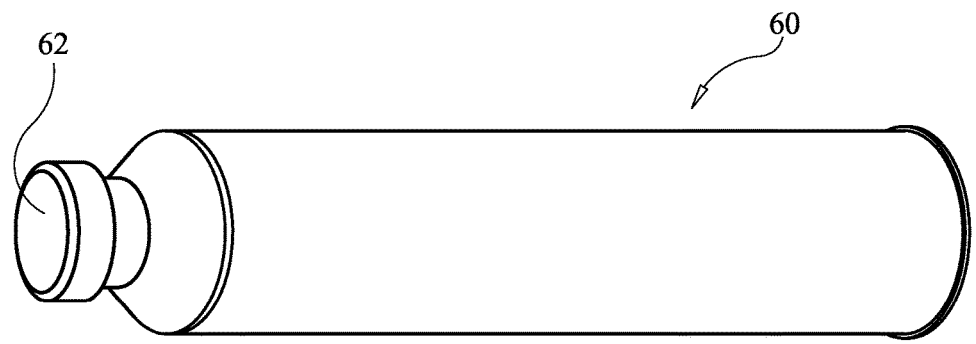
FIG. 8 is an isolated perspective view of the dispenser's vial in its sealed state.
Figure 9:
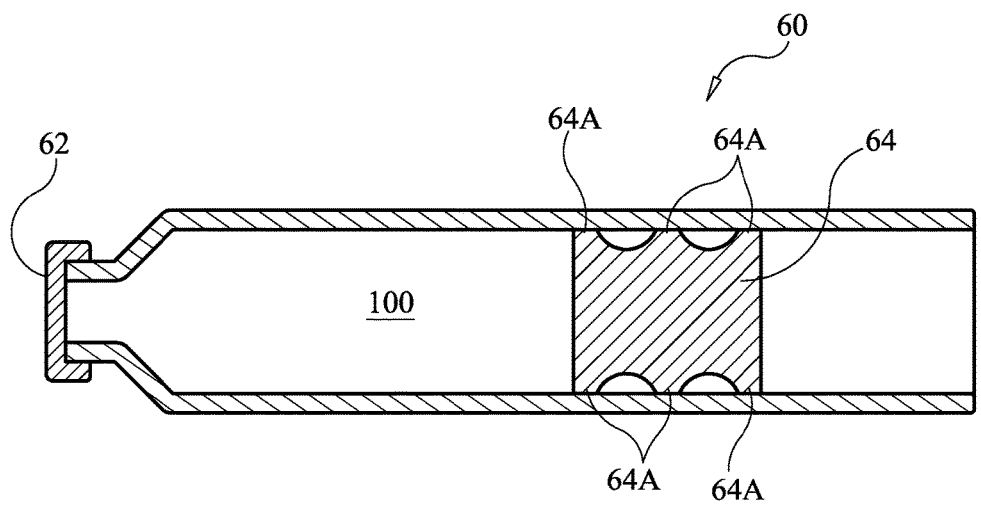
FIG. 9 is an axial cross-sectional view of the vial in its sealed state.

Referring now to the drawings, simultaneous reference will be made to FIGS. 1-10 where an assembled multi-mode medication dispenser in accordance with an embodiment of the present invention is shown in FIG. 1 and its various components are shown in isolated views in FIGS. 1A-10. The assembled medication dispenser is referenced generally by numeral 10. As will be explained further below, medication dispenser 10 is pre-filled with a fluid medicine 100 that can be dispensed to a patient (not shown) in a variety of delivery modes. For example, medicine 100 could be delivered via an atomizer, an injection needle, an intravenous drip line, etc. In the illustrated embodiment, medication dispenser 10 is constructed to permit a delivery mode's appropriate attachment to be coupled to medication dispenser 10 at time of use.

Figure 10:
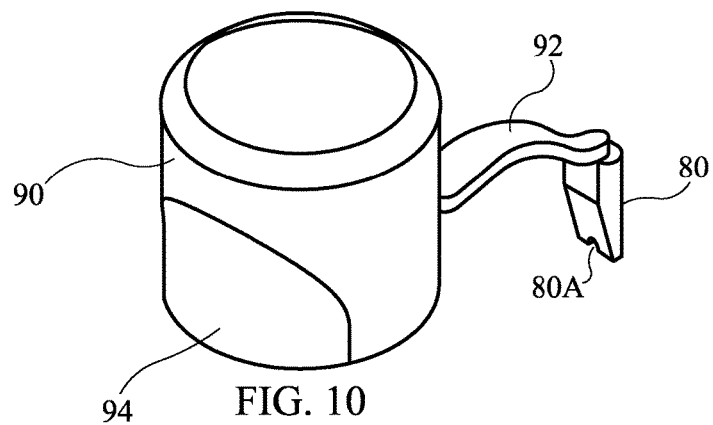
FIG. 10 is an isolated perspective view of the dispenser's cap and restrainer.

Medication dispenser 10 includes a hollow body 20 (FIGS. 2-4), a plunger body 40 (FIGS. 5-7), a vial 60 used to hold medicine 100 (FIGS. 8-9), and an axial restrainer 80 that can be tethered to a cap 90 (FIG. 10). Each of the above components will be described for the illustrated embodiment of medication dispenser 10. However, it is to be understood that some of the features described herein can be omitted and/or can be realized in a variety of ways without departing from the scope of the present invention.

Hollow body 20 is made from a rigid material (e.g., plastic, metal, composite, etc.) and can be cylindrical as shown. One end 22 of hollow body 20 is open and the opposing end 24 thereof is sealed with a luer fitting 26 that will be explained further below. Luer fitting 26 can be attached to or integrated with end 24 without departing from the scope of the present invention. An open-ended rigid and hollow tube 28 is supported in luer fitting 26. More specifically and with reference to FIG. 1A, tube 28 has one open end 28A disposed in hollow body 20 and its opposing open end 28B disposed in luer fitting 26. Open end 28A can be pointed (as shown) for reasons that will be explained further below.

The exterior surface of hollow body 20 can have one or more axially-extending guides 30 (e.g., raised ridges as shown) for engaging plunger body 40 as will be explained later herein. Hollow body 20 can also have a radial hole 32 for receiving axial restrainer 80. A window 34 can also be provided in hollow body 20 such that a portion of vial 60 containing medicine 100 can be viewed. One or more stops 36 can also be provided on the exterior surface of hollow body 20. As will be explained further below, stops 36 define one or more axial locations on hollow body 20 that will engage with a portion of plunger body 40 to define, for example, initial, intermediate, and stopping positions of plunger body 40. Movement of plunger body 40 past both the initial and intermediate positions is accomplished by the application of sufficient force to the end of plunger body 40 as will be explained further below.

Plunger body 40 is also made from a rigid material (e.g., plastic, metal, composite, etc.) that can be the same or different than the material used for hollow body 20. In general, plunger body 40 is sized/shaped to form a sliding indexed fit with the exterior surface of hollow body 20. For example, if hollow body 20 is cylindrical, the interior surface of plunger body 40 will also be cylindrical as is the case in the illustrated embodiment. Plunger body 40 has an open-end 42 sized/shaped to engage/receive open end 22 of hollow body 20. The opposing end 44 of plunger body 40 is closed. The exterior portion 44A of closed end 44 can define a depression that will be engaged by a person's thumb during dispensing of the medication. A rod 46 coupled to or integrated with closed end 44 extends axially along and within plunger body 40. Rod 46 can be hollow (as shown) or solid without departing from the scope of the present invention. Rod 46 terminates in an outboard end 46A that can be closed or open (as shown) without departing from the scope of the present invention.

Plunger body 40 can also include features that cooperate with some of the above-described features of hollow body 20. For example, inner surfaces of plunger body 40 can have axial channels 48 defined therein where channels 48 are indexed to guides 30 on hollow body 20. Channels 48 are sized/shaped for sliding engagement with guides 30. Open end 42 can have axial slits 50 defined therein to thereby define spring arms 52. The outboard end of each spring arm 52 has tab 54 configured to engage stops 36 on hollow body 20 as will be explained further below.

Vial 60 can be made from a rigid material that is generally transparent or translucent such that medicine 100 can be viewed from the outside of vial 60. One end of vial 60 is sealed with a rupturable seal 62 and the other end of vial 60 is sealed with a piston 64 that is capable of axial movement within vial 60 while maintaining a seal therewith. Piston 64 can be made from a semi-rigid material (e.g., rubber) and configured to include annular ridges 64A that essentially function like o-rings to form a seal with the interior surface of vial 60. Separate o-rings (not shown) could be used in addition to or in place of annular ridges 64A without departing from the scope of the present invention. Piston 64 can be positioned partially within vial 60 (as shown) or at the end thereof depending on the amount of medicine 100 to be contained within vial 60.

Vial 60 is sized/shaped such that it can slide axially within hollow body 20. When medication dispenser 10 is in its assembled form, seal 62 is adjacent to open end 28A of open-ended tube 28. Plunger body 40 is then slid over hollow body 20 until tabs 54 engage the first set of tabs 36 on hollow body 20 to thereby place plunger body 40 in its initial position. Outboard end 46A of rod 46 is sized to fit within vial 60 in order to engage piston 64 at the point where it seals vial 60.

Prior to use, it may be necessary to restrain vial 60 from axial movement within hollow body 20 to thereby prevent inadvertent puncturing of rupturable seal 62 by open end 28A of tube 28. Accordingly, axial restrainer 80 is inserted into hollow body 20 via radial hole 32 in order to keep vial 60 from axial movement towards open end 28A and/or serve as a block between open end 28A and rupturable seal 62. Axial restrainer 80 can include a cradle 80A that seats on tube 28. Axial restrainer 80 protrudes from hollow body 20 to facilitate its removal prior to using dispenser 10.

Cap 90 is a protective (e.g., rigid material) covering for luer fitting 26. That is, cap 90 is releasably coupled to luer fitting 26 such that it remains in place prior to use, but can be readily removed when dispenser 10 is to be used. It is to be understood that the particular type of releasable coupling between cap 90 and luer fitting 26 is not a limitation of the present invention. Cap 90 can be tethered to axial restrainer 80 by an integral tether 92. In this way, when cap 90 is removed, cap 90 can secondarily serve as a grip for the removal of axial restrainer 80. Cap 90 can include a depressed region 94 so that a user can use their thumb to push cap 90 off of luer fitting 26.

Figure 11:
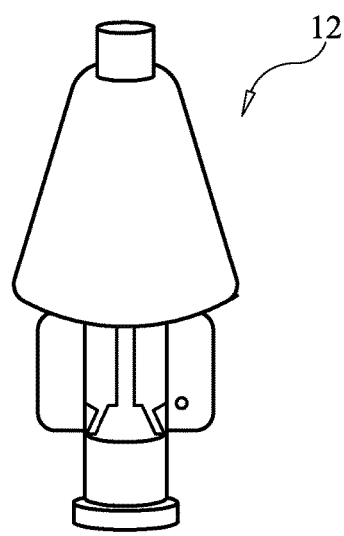
FIG. 11 is a side view of an atomizer for coupling to the dispenser's open-ended tube.
Figure 12:
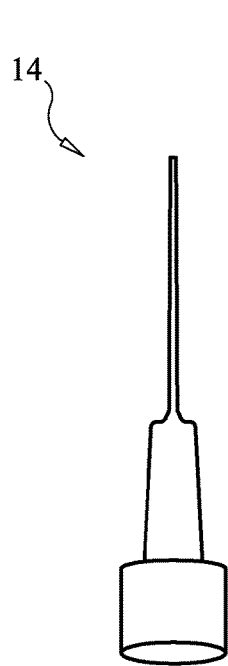
FIG. 12 is a side view of an injection needle for coupling to the dispenser's open-ended tube.
Figure 13:
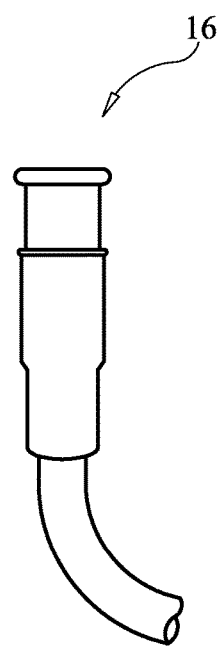
FIG. 13 is a side view of a portion of an intravenous drip line for coupling to the dispenser's open-ended tube.

As just described, once cap 90 is removed, luer fitting 26 is ready to receive and cooperate with an attachment that will couple to luer fitting 26 and open end 28B of tube 28. For example, the attachment can be an atomizer 12 (FIG. 11), an injection needle 14 (FIG. 12), or an intravenous drip line 16 (FIG. 13). The various attachments, luer fitting 26, and the mechanisms used for their cooperative attachment are well known in the art. After a selected attachment is coupled to open end 28B of tube 28, cap 90 can be used to pull axial restrainer 80 out of hollow body 20. Once this occurs, axial pressure can be applied to closed end 44 of plunger body 40 (e.g., against depression 44A) as indicated by arrow 200 (FIG. 1). Once pressure 200 is sufficient, tabs 54 will spring radially away from hollow body 20 to clear the first stops 36. As outboard end 46A of rod 46 engages piston 64, vial 60 is moved axially towards open end 28A of tube 28. As axial movement of vial 60 continues, open end 28A pushes through seal 62. The ruptured opening of seal 62 is limited to the diameter of tube 28 by making open end 28A pointed as shown. Once vial 60 engages end 24 of hollow body 20 (i.e., bottoms out in hollow body 20) and pressure 200 is continually applied, rod 46 drives piston 64 into vial 60 thereby pressurizing medicine 100 in vial 60 to force it out through tube 28 and through one of the attachments coupled to open end 28B. Medicine 100 can be completely dispensed or partially dispensed. For example, if additional/intermediate stops 36 are provided on hollow body 20 as is the case in the illustrated embodiment, the positions of the additional/intermediate stops can be calibrated to predetermined dosing levels of medicine 100.

The advantages of the present invention are numerous. The medication dispenser is pre-filled with medicine and is protected from inadvertent dispensing prior to use. The dispenser can be outfitted with a delivery mode attachment of choice thereby making the dispenser suitable for use in a variety of applications. The dispenser provides crush-resistant and robust packaging, and a versatile multi-mode dispensing capability that will make it an invaluable addition to the practice of emergency medicine and/or field medicine.

Since the medication dispenser is completely self-contained, it can be used in low-light or no-light environments.

Although the invention has been described relative to a specific embodiment thereof, there are numerous variations and modifications that will be readily apparent to those skilled in the art in light of the above teachings. For example, a delivery vehicle attachment could be pre-attached to open end 28B. The assembled medication dispenser could also be packaged in an outer hard shell for additional pre-use protection. It is therefore to be understood that, within the scope of the appended claims, the invention may be practiced other than as specifically described.

What is claimed as new and desired to be secured by Letters Patent of the United States is:

1. A medication dispenser, comprising:
    a hollow body having a first end and a second end opposing said first end, said first end being open;
    a hollow open-ended tube coupled to said second end of said hollow body;
    a vial having one end sealed with a piston and one end sealed with a rupturable element, said vial slidably disposed in said hollow body with said rupturable element adjacent to one open end of said tube;
    a restrainer disposed in said hollow body for preventing sliding movement of said vial in said hollow body, said restrainer extending partially from said hollow body; and
    a plunger body indexed to an outer surface of said hollow body for axial movement with respect thereto, said plunger body including a rod disposed therein for engaging said piston.

2. A medication dispenser as in claim 1, wherein said outer surface of said hollow body defines a plurality of stops disposed axially along said hollow body for engagement by a portion of said plunger body, wherein said axial movement of said plunger body is defined in increments in correspondence with said stops.

3. A medication dispenser as in claim 1, further comprising a luer fitting coupled to said second end of said hollow body for supporting a portion of said tube therein.

4. A medication dispenser as in claim 3, further comprising a cap releasably coupled to and covering said luer fitting.

5. A medication dispenser as in claim 1, further comprising one of an atomizer, an injection needle, and an intravenous drip line coupled to another open end of said tube.

6. A medication dispenser as in claim 1, further comprising medicine in said vial.

7. A medication dispenser as in claim 1, wherein said hollow body includes a window through which a portion of said vial is visible.

8. A medication dispenser, comprising:
    a cylindrical hollow body having a plurality of guides defined axially along an outer surface of said hollow body, said hollow body having a first end and a second end opposing said first end, said first end being open;
    a hollow open-ended tube coupled to said second end of said hollow body;
    a vial having one end sealed with a piston and one end sealed with a rupturable element, said vial slidably disposed in said hollow body with said rupturable element adjacent to an open end of said tube; and
    a cylindrical plunger body having an open end and a closed end, said plunger body having a rod coupled to said closed end and extending axially along and inside of said plunger body, said plunger body fitted over said hollow body and indexed to said guides thereon for axial movement with respect to said hollow body, said rod having an outboard end for engaging said piston.

9. A medication dispenser as in claim 8, further comprising a restrainer disposed in said hollow body for preventing sliding movement of said vial in said hollow body, said restrainer extending partially from said hollow body.

10. A medication dispenser as in claim 8, wherein said outer surface of said hollow body defines a plurality of stops disposed axially along said hollow body for engagement by a portion of said plunger body, wherein said axial movement of said plunger body is defined in increments in correspondence with said stops.

11. A medication dispenser as in claim 8, further comprising a luer fitting coupled to said second end of said hollow body for supporting a portion of said tube therein.

12. A medication dispenser as in claim 11, further comprising a cap releasably coupled to and covering said luer fitting.

13. A medication dispenser as in claim 8, further comprising one of an atomizer, an injection needle, and an intravenous drip line coupled to another open end of said tube.

14. A medication dispenser as in claim 8, further comprising medicine in said vial.

15. A medication dispenser as in claim 8, wherein said hollow body includes a window through which a portion of said vial is visible.

16. A medication dispenser, comprising:
    a hollow body having a plurality of guides defined axially along an outer surface of said hollow body, said hollow body having a first end and a second end opposing said first end, said first end being open;
    a luer fitting coupled to said second end of said hollow body;
    a hollow open-ended tube supported in said luer fitting, wherein a first open end of said tube is pointed and is disposed in said hollow body and a second open end of said tube is disposed in said luer fitting;
    a vial having one end sealed with a piston and one end sealed with a rupturable element, said vial slidably disposed in said hollow body with said rupturable element adjacent to said first open end of said tube;
    a cylindrical plunger body having an open end and a closed end, said plunger body having a rod coupled to said closed end and extending axially along and inside of said plunger body, said plunger body fitted over said hollow body and indexed to said guides thereon for axial movement with respect to said hollow body, said rod having an outboard end for engaging said piston;
    a restrainer disposed in said hollow body for preventing sliding movement of said vial in said hollow body, said restrainer having an exposed portion thereof extending partially from said hollow body; and
    a cap releasably coupled to and covering said luer fitting, said cap tethered to said exposed portion of said restrainer.

17. A medication dispenser as in claim 16, wherein said outer surface of said hollow body defines a plurality of stops disposed axially along said hollow body for engagement by a portion of said plunger body, wherein said axial movement of said plunger body is defined in increments in correspondence with said stops.

18. A medication dispenser as in claim 16, further comprising one of an atomizer, an injection needle, and an intravenous drip line coupled to said second open end of said tube.

19. A medication dispenser as in claim 16, further comprising medicine in said vial.

20. A medication dispenser as in claim 16, wherein said hollow body includes a window through which a portion of said vial is visible.

* * * * *